United States Patent [19]

Mandal et al.

[11] Patent Number: 6,117,278
[45] Date of Patent: Sep. 12, 2000

[54] METHOD OF MAKING α-CHLOROXYLENES

[75] Inventors: Sanjay Mandal, Grand Island; Kevin R. Benson, West Seneca; Michael J. Fifolt; John Hickey, both of Grand Island; James Franc, North Tonawanda; George Piotrowski, Cheektowaga; William S. Derwin, Grand Island, all of N.Y.

[73] Assignee: Occidental Chemical Corporation, Dallas, Tex.

[21] Appl. No.: 09/208,676

[22] Filed: Dec. 10, 1998

[51] Int. Cl.[7] .......................... C07C 17/00; C07C 22/00; C07C 25/00
[52] U.S. Cl. .................... 204/157.99; 570/207; 570/208; 570/209; 570/210
[58] Field of Search ........................ 204/157.99; 570/101, 570/144, 193, 207, 208, 209, 210

[56] References Cited

U.S. PATENT DOCUMENTS

| | | | |
|---|---|---|---|
| 3,442,960 | 5/1969 | De Puy et al. | 260/651 |
| 4,048,033 | 9/1977 | Yoshinaka et al. | 204/158 HA |
| 5,080,767 | 1/1992 | Ando et al. | 204/158.1 |
| 5,145,996 | 9/1992 | Jacobson et al. | 564/98 |

FOREIGN PATENT DOCUMENTS

| 2629248 | 1/1978 | Germany . |
|---|---|---|
| 6340562 | 12/1994 | Japan . |

*Primary Examiner*—Kathryn Gorgos
*Assistant Examiner*—Edna Wong
*Attorney, Agent, or Firm*—Richard D. Fuerle; Anne E. Brookes

[57] ABSTRACT

Disclosed is a method for making high purity α-chloroxylenes. A composition is formed of about 15 to about 80 wt % of a xylene and about 20 to about 85 wt % of a solvent. The solvent can be toluene, ring halogenated toluene, benzotrichloride, ring halogenated benzotrichloride, benzotrifluoride, ring halogenated benzotrifluoride, α,α,α,α',α',α'-hexafluorometaxylene, α,α,α,α',α',α'-hexafluoroparaxylene, or a mixture thereof. The composition is heated to about 70 to about 160° C. No base is present in the composition. Chlorine gas is sparged through the composition and chlorine free radicals are generated therein. The chlorine free radicals can be generated either with UV light or by means of a chlorine free radical initiator.

20 Claims, No Drawings

METHOD OF MAKING α-CHLOROXYLENES

CROSS REFERENCE TO RELATED APPLICATION

This application is related to application Ser. No. 09/209,030, filed of even date by S. Mandal et al., titled, "Method of Making α-Chloro-α,α-Difluoro Aromatic Compounds." still pending.

BACKGROUND OF THE INVENTION

This invention relates to the reaction of xylene with chlorine gas to produce α-chloroxylenes. In particular, it relates to performing the reaction in a solvent of toluene, ring halogenated toluene, benzotrichloride (BTC), ring halogenated BTC, benzotrifluoride (BTF), ring halogenated BTF, α,α,α,α',α',α'-hexafluorometaxylene (HFMX), α,α,α,α',α',α'-hexafluoroparaxylene (HFPX), or a mixture thereof to minimize ring chlorination. α,α,α,α',α',α'-Hexachloroparaxylene (HCPX) is an important chemical intermediary used to make herbicides and other products. High purity (>99%) HCPX is required for many applications. HCPX can be made by reacting p-xylene with chlorine gas in a solvent. For example, JP6-340562 discloses that process using a base and a solvent of a chlorinated benzotrifluoride, such as parachlorobenzotrifluoride, to produce 99% pure HCPX. Washing to remove impurities, however, was required to obtain that level of purity. The use of a base and the subsequent washing step add to the cost of producing the HCPX.

SUMMARY OF THE INVENTION

We have discovered that a-chlorinated xylenes can be made in a solvent of toluene, ring halogenated toluene, BTC, ring halogenated BTC, BTF, ring halogenated BTF, HFMX, or HFPX. Surprisingly, we are able to obtain a purity of at least 99% without using a base and without washing the product, thereby eliminating these additional steps. Because of the high purity achieved, no further purification steps are required.

DESCRIPTION OF THE PREFERRED EMBODIMENTS

The substrates used in the process of this invention are metaxylene, paraxylene, and mixtures thereof. Paraxylene is preferred as it is commercially more important.

The reaction is performed in a solvent of toluene, ring halogenated toluene, BTC, ring halogenated BTC, BTF, ring halogenated BTF, HFMX, HFPX, or a mixture thereof. Unlike many other solvents, these solvents will not be fluorinated in hydrogen fluoride (except for BTC, which is fluorinated to BTF), an important consideration if the α-chloroxylene is subsequently fluorinated. Toluene, ring halogenated toluene, BTF, and HFPX are preferred.

A means for generating chlorine free radicals is also needed. Either ultraviolet (UV) light or a chlorine free radical initiator can be used. A chlorine free radical initiator offers greater control of the reaction but UV light does not introduce other substances into the reaction. Examples of chlorine free radical initiators include α,α'-azobisisobutyronitrile (AIBN), α,α'-azobis(cyclohexanecarbonitrile) (sold by Dupont as "VAZO-88"), benzoyl peroxide, cumene hydroperoxide, and t-butyl hydroperoxide. The preferred initiator is "VAZO-88" because it has a long half life of 10 hours at 88° C., a preferred reaction temperature.

In the process of this invention, a composition is formed of about 15 to about 80 wt % of a xylene, about 20 to about 80 wt % of a solvent, and, if a chlorine free radical generator is used instead of ultraviolet light, about 0.5 to about 3 wt % of the chlorine free radical generator. If more solvent is used, the throughput is reduced and less solvent will increase ring chlorination. Less free radical generator increases the reaction time and reduces throughput and more is unnecessary. Preferably, a composition is formed of about 25 to about 50 wt % of the xylene, about 50 to about 75 wt % of a solvent, and, if a free radical generator is used, about 1 to about 2 wt % of the free radical generator. No base is added to the composition or the reaction.

The composition is heated to a temperature of about 70 to about 160° C. There is less ring chlorination at higher temperatures and the reaction is faster, but the solubility of chlorine is reduced, which prolongs the reaction time and reduces throughput. The preferred temperature range is about 65 to about 120° C. and the best results were obtained at a temperature range of about 80 to about 90° C. Heating at reflux is also preferred as that reduces ring chlorination. At a temperature of about 85° C., the reaction normally takes about 10 hours. No pressure is required for the reaction.

Chlorine gas is sparged through the heated composition. The amount of chlorine gas used determines the number of α-hydrogens replaced with chlorines. About 0.9 to about 1.5 equivalents of chlorine should be used for each α-hydrogen to be replaced; less chlorine will not complete the reaction and more chlorine is unnecessary. Preferably, all α-hydrogens are replaced with chlorine. If chlorine gas breaks through the composition prior to completion of the reaction, additional initiator can be added. If further chlorine breakthrough occurs, the reaction is complete. The solvent is filtered off, but washing the product to increase purity is normally unnecessary.

An important product made from the HCPX is α,α'-dichloro-α,α,α',α',-tetrafluoroparaxylene (DCTFPX). See co-pending U.S. patent application Ser. No. 09/209,030, filed of even date, titled "Method of Making α-Chloro-α,α-Difluoro Aromatic Compounds", herein incorporated by reference. In that reaction, HCPX is reacted with hydrogen fluoride in the presence of a catalyst to produce DCTFPX. The reaction to produce DCTFPX can be performed without removing the solvent used to make HCPX. DCTFPX is used as a precursor for an inter-layer dielectric material for making semiconductor chips. It is also a precursor for inert and transparent conformal coatings for electrical components.

The following examples further illustrate this invention.

EXAMPLE 1

500 g of BTF and 170 g of p-xylene were placed in a 1 L jacketed glass photochlorination apparatus equipped with a 100 W medium pressure Hanovia UV light (air cooled), a reflux condenser, a thermocouple, and an inlet for chlorine. Using some thermal tape around the apparatus and a light, the reactor was heated to 65–70° C. The chlorine flow was started at 100 mL/min and slowly increased to 1000 mL/min. The temperature of the reactor was maintained between 85–90° C., while the condenser temperature was at −25° C. throughout the reaction. The chlorine was added until the reaction was complete, in 9.5 hours. A total of 940.6 g of the mixture of HCPX and BTF was discharged from the reactor while maintaining the reactor temperature at 90° C. Solid HCPX can be obtained by filtering off the solvent. An assay of the final mixture, excluding the peak due to solvent, by gas chromatography (GC) indicated 99% HCPX. The overall isolated yield of HCPX was 88%. The overall chlorine efficiency was 92%.

EXAMPLE 2

Example 1 was repeated using 400 g of BTF and 135.8 g of p-xylene. The reactor was heated to reflux (108–120° C.) and chlorine flow was started at 350 mL/min and slowly increased to 500 mL/min. The temperature of the reactor was maintained between 108 and 120° C., while the condenser temperature was at −25° C. throughout the reaction. The reaction was complete in 49 hours, of which 20 hours were spent for the last one equivalent chlorination. A total of 761 g of the mixture of HCPX and BTF was discharged from the reactor while maintaining the reactor temperature at 90° C. An assay of the final mixture by GC indicated 99% HCPX. The overall isolated yield of HCPX was 94%. No significant amount of ring-chlorinated or polymerized products was observed. The overall chlorine efficiency was 54%. This example shows that heating at reflux improved yield.

EXAMPLE 3

Example 1 was repeated using 500.5 g of BTF and 170.1 g of p-xylene. The temperature of the reactor was maintained at 75° C. while the condenser temperature was at −25° C. throughout the reaction. The reaction was complete in 8 hours. A total of 962 g of the mixture of HCPX and BTF was discharged from the reactor while maintaining the reactor temperature at 90° C. An assay of the final mixture by GC indicated 98.45% HCPX. The overall isolated yield of HCPX was 90%. The overall chlorine efficiency was 82%. This example shows that at a lower temperature more ring-chlorinated products are formed.

EXAMPLE 4

Into a 2 L reactor equipped with a reflux condenser, a thermocouple, and an inlet for chlorine were placed 360.8 g of p-xylene, 1060 g of BTF, and 1.3 g of "VAZO-88." The reactor was heated to 70° C., using some thermal tape around the apparatus and a light. The chlorine flow was started at 500 mL/min and slowly increased to 1500 mL/min. The temperature of the reactor was maintained between 85–90° C. while the condenser temperature was at −25° C. throughout the reaction. Whenever chlorine efficiency was decreasing, 1500–2000 ppm of fresh "VAZO-88" were added to the reactor. A total of 7.97 g of "VAZO-88" (2.21 wt % of p-xylene used) was added over the course of the reaction. An increase in chlorine utilization was observed following "VAZO-88" additions. The chlorine was added until the reaction was complete, in 25.5 hours. A total of 2077 g of the mixture of HCPX and BTF was discharged from the reactor while maintaining the reactor temperature at 90° C. An assay of the final mixture by GC indicated 99% HCPX. The overall isolated yield of HCPX was 95.6%. No significant amount of ring-chlorinated or polymerized products was observed. The overall chlorine efficiency was 70.79%. This example shows that the reaction takes longer when a radical initiator is used than when UV light is used at the same temperature.

We claim:

1. A method of making an α-chloroxylene comprising
    (A) forming a composition of
        (1) about 15 to about 80 wt % of a xylene; and
        (2) about 20 to about 80 wt % of a solvent selected from the group consisting of toluene, ring halogenated toluene, benzotrichloride, ring halogenated benzotrichloride, benzotrifluoride, ring halogenated benzotrifluoride, α,α,α, α',α',α'-hexafluoroparaxylene, α,α,α,α',α',α'-hexafluorometaxylene, and mixtures thereof, where no base is present in said composition;
    (B) heating said composition to about 70 to about 160° C.;
    (C) sparging chlorine gas therethrough; and
    (D) generating chlorine free radicals in said composition from said chlorine gas.

2. A method according to claim 1 wherein said xylene is p-xylene.

3. A method according to claim 1 wherein said xylene is m-xylene.

4. A method according to claim 1 wherein said solvent is benzotrifluoride.

5. A method according to claim 1 wherein said solvent is toluene or a ring halogenated toluene.

6. A method according to claim 1 wherein said solvent is α,α,α,α',α',α'-hexafluoroparaxylene.

7. A method according to claim 1 wherein said solvent is α,α,α,α',α',α'-hexafluorometaxylene.

8. A method according to claim 1 wherein said heating is at about 80 to about 90° C.

9. A method according to claim 1 wherein said α-chloroxylene is α,α,α, α',α',α'-hexachloroparaxylene.

10. A method according to claim 9 including the additional last step of reacting said α,α,α,α',α',α'-hexachloroparaxylene with hydrofluoric acid to form α,α'-dichloro-α,α,α',α'-tetrafluoroparaxylene.

11. A method according to claim 1 wherein said chlorine free radicals are generated using UV light.

12. A method according to claim 1 wherein said chlorine free radicals are generated using about 0.5 to about 3 wt % of a chlorine free radical initiator in said composition.

13. A method according to claim 12 including the step of adding additional initiator when chlorine breaks through.

14. A method according to claim 1 wherein said solvent is benzotrichloride.

15. A method of making α, α, α, α',α',α'-hexachloroparaxylene comprising
    (A) forming a composition of
        (1) about 25 to about 50 wt % p-xylene; and
        (2) about 50 to about 75 wt % of a solvent selected from the group consisting of toluene, ring halogenated toluene, benzotrifluoride, α,α,α,α',α',α'-hexafluoroparaxylene, and mixtures thereof; and
        (3) about 1 to about 2 wt % of a chlorine free radical initiator, where no base is present in said composition;
    (B) heating said composition at about 65 to about 120° C.; and
    (C) sparging chlorine gas therethrough.

16. A method according to claim 15 including the additional last step of reacting said α, α, α, α',α',α'-hexachloroparaxylene with hydrogen fluoride to form α,α'-dichloro-α,α,α',α'-tetrafluoroparaxylene.

17. A method according to claim 16 wherein said additional last step is performed without removing said solvent.

18. A method of making α,α,α,α',α',α'-hexachloroparaxylene comprising
    (A) forming a composition of
        (1) about 25 to about 50 wt % p-xylene; and
        (2) about 50 to about 75 wt % of a solvent selected from the group consisting of toluene, ring halogenated toluene, benzotrifluoride, α,α,α,α',α',α'-hexachloroparaxylene, and mixtures thereof, where no base is present in said composition;

(B) heating said composition at about 80 to about 90° C.;

(C) sparging chlorine gas therethrough; and (D) exposing said chlorine gas to ultraviolet light to form chlorine free radicals.

19. A method according to claim 18 including the additional last step of reacting any $\alpha,\alpha,\alpha,\alpha',\alpha',\alpha'$-hexachloroparaxylene present with hydrogen fluoride to form $\alpha,\alpha'$-dichloro-$\alpha,\alpha,\alpha',\alpha'$-tetrafluoroparaxylene.

20. A method according to claim 19 wherein said additional last step is performed without removing said solvent.

* * * * *

UNITED STATES PATENT AND TRADEMARK OFFICE
CERTIFICATE OF CORRECTION

PATENT NO. : 6,117,278
DATED : September 12, 2000
INVENTOR(S) : Sanjay Mandel et al.

It is certified that error appears in the above-identified patent and that said Letters Patent is hereby corrected as shown below:

In the Claims

Claim 18, column 4, line 66, delete "$\alpha,\alpha,\alpha,\alpha',\alpha',\alpha'$-hexachloroparaxylene" and substitute -- $\alpha,\alpha,\alpha,\alpha',\alpha',\alpha'$-hexafluoroparaxylene --

Signed and Sealed this

Twenty-ninth Day of May, 2001

Attest:

NICHOLAS P. GODICI

*Attesting Officer*  *Acting Director of the United States Patent and Trademark Office*